(12) United States Patent
Kawabe et al.

(10) Patent No.: US 7,980,140 B2
(45) Date of Patent: Jul. 19, 2011

(54) ADHESION INSPECTION APPARATUS AND ADHESION INSPECTION METHOD USING THE SAME

(75) Inventors: Hideyuki Kawabe, Gunma (JP); Katsushige Mori, Yokohama (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 198 days.

(21) Appl. No.: 12/374,570

(22) PCT Filed: Jul. 23, 2007

(86) PCT No.: PCT/JP2007/064829
§ 371 (c)(1),
(2), (4) Date: Jan. 21, 2009

(87) PCT Pub. No.: WO2008/013292
PCT Pub. Date: Jan. 31, 2008

(65) Prior Publication Data
US 2009/0266174 A1   Oct. 29, 2009

(30) Foreign Application Priority Data
Jul. 25, 2006   (JP) ................................. 2006-201402

(51) Int. Cl.
*G01N 3/24*   (2006.01)
(52) U.S. Cl. ........................................ 73/842
(58) Field of Classification Search .............. 73/842, 73/774
See application file for complete search history.

(56) References Cited

U.S. PATENT DOCUMENTS

| | | | | |
|---|---|---|---|---|
| 3,583,124 A | * | 6/1971 | Morrison | 53/492 |
| 4,318,265 A | * | 3/1982 | Orsinger et al. | 53/492 |
| 4,776,152 A | * | 10/1988 | Kruk | 53/492 |
| 4,835,941 A | * | 6/1989 | Torii et al. | 53/382.1 |
| 4,862,740 A | | 9/1989 | Lanier | |

(Continued)

FOREIGN PATENT DOCUMENTS

CN   2359685 Y   1/2001

(Continued)

OTHER PUBLICATIONS

International Search Report issued on Nov. 16, 2007 for International PCT Application PCT/JP2007/064829 filed Jul. 23, 2007.

*Primary Examiner* — Lisa M Caputo
*Assistant Examiner* — Octavia Davis
(74) *Attorney, Agent, or Firm* — Drinker Biddle & Reath LLP

(57) ABSTRACT

An object of the present invention is to provide an adhesion inspection apparatus and method that can provide a reliable detection even for defect without the need of any complicated works, such as adjusting of an optical axis of instrument. An adhesion inspection apparatus 1 for inspecting adhesion of a package box 3 constructed with use of an adhesive, said apparatus characterized in that a vacuum pad 5 to be affixed for sucking on an outer surface of the package box 3 at an area proximal to an adhered region thereof; an inspection arm 9 carrying the vacuum pad 5 at one end thereof; a rotating shaft 11 joined to the other end of the inspection arm 9; a driving device 13 for driving the rotating shaft 11 to make a rotational movement; and a torque sensor 15 for detecting a torque induced in the driving device 13.

13 Claims, 4 Drawing Sheets

U.S. PATENT DOCUMENTS

| | | | |
|---|---|---|---|
| 5,111,701 A | | 5/1992 | Klein |
| 5,404,751 A | * | 4/1995 | Beran et al. ................. 73/150 A |
| 5,581,972 A | * | 12/1996 | Antonelli ............................ 53/75 |
| 6,293,076 B1 | * | 9/2001 | Miller et al. .................... 53/460 |
| 6,802,214 B2 | * | 10/2004 | Kebart et al. ............... 73/150 A |

FOREIGN PATENT DOCUMENTS

| | | |
|---|---|---|
| FR | 2 753 532 | 3/1998 |
| JP | 1-107506 | 7/1989 |
| JP | 2005-104568 | 4/2005 |

* cited by examiner

ADHESION INSPECTION APPARATUS AND ADHESION INSPECTION METHOD USING THE SAME

CROSS REFERENCE TO RELATED APPLICATIONS

This application is the National Stage of International Application No. PCT/JP2007/064829, filed Jul. 23, 2007, and claims benefit of Japanese Application No. 2006-201402, filed Jul. 25, 2006, both of which are herein incorporated by reference in their entirety.

FIELD OF THE INVENTION

The present invention relates to an adhesion inspection apparatus and method for inspecting of a package box constructed with use of an adhesive.

BACKGROUND OF THE INVENTION

To give an example, when a package box is constructed with corrugated cardboard, a subject to be packed is placed in a box body, and then flaps of the package box are applied with an adhesive, such as a hot-melt adhesive, with which the flaps adhere to each other with one over the other to close the package box. To do this, it is necessary that the flaps are reliably adhered to each other with the adhesive.

There are some methods for indirectly determining the adhesion in conjunction with a conventional adhesion inspection apparatus. One such adhesion inspection apparatus detects, for example, an amount of applied adhesive, a temperature of the adhesive, a position and an extent of the application, etc., with use of a camera or an infrared sensor so as to estimate the adhesion.

In addition, as a technique to inspect the adhesion directly, a defective sealing inspecting device for a package box has been disclosed (see Japanese Patent Public disclosure No. 2005-104568). The defective sealing inspecting device has: a lid sucking path La, including a lid sucking tool 31 arranged along a box conveying path; a lid sucking tool transfer device 30 making a circular movement along a lid lifting path Lb, disposed following to the lid sucking path La and out from the box conveying path; and a lid detection sensor 50 for detecting a top surface of a lid 3 that has been peeled away from a box body 2 and lifted up by a lifting force exerted on the lid 3 from the lid sucking tool 31 disposed in the lid lifting path Lb. When such a sealing inspecting device is used, if the lid 3 is in a defective adhesion condition, the lid 3 would be separated from the box 2 and lifted up, and thus lifted-up lid 3 is then detected by a detection device, such as an optical sensor, ultimately enabling the inspection of the defective sealing (adhesion) condition.

SUMMARY OF THE INVENTION

However, there are some shortcomings in connection with those conventional adhesion inspecting devices, as will be described below. Specifically, the use of the indirect method for estimating the adhesion fails to figure out the adhesion accurately. In addition, in the foregoing example of the direct inspection according to the prior art, the inspection can be only effective when the lid 3 is fully peeled away from the box body 2, but the inspection could be ineffective for defect with poor adhesion. Specifically, for the case of poor adhesion, the lid could be peeled away from the box body 2 possibly after the inspection, meaning that the inspection could not work well on such defect case. In addition, using the optical sensor and the like to detect the lifted-up lid 3 for the inspection of the defective adhesion necessitates a complicated work, such as adjusting an optical axis of a device constructing the sensor.

An object of the present invention is to provide an adhesion inspection apparatus and method that could overcome the shortcomings in conjunction with those conventional adhesion inspection apparatuses, and particularly that can provide a reliable inspection of the defect without the need for the complicated work, such as the adjusting of the optical axis of the device.

PREFERRED EMBODIMENTS OF THE INVENTION

An embodiment of the present invention will now be described with reference to the attached drawings.

[Overview]

Figure 1:
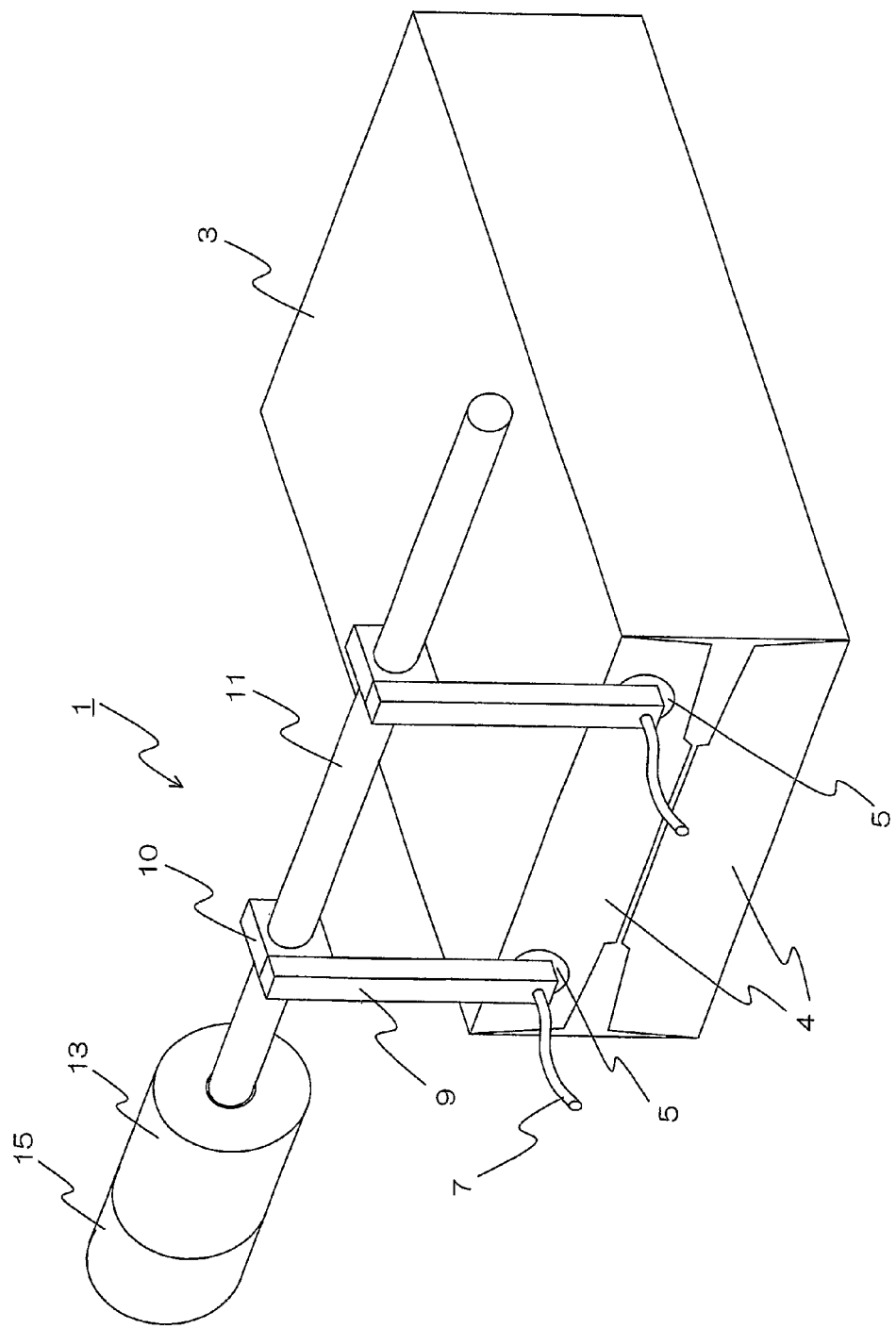
FIG. 1 is a schematic perspective view of an adhesion inspection apparatus according to an embodiment of the present invention.

Referring first to FIG. 1, an overview of an adhesion inspection apparatus 1 according to the embodiment is shown in a perspective view. As shown in this FIG. 1, the adhesion inspection apparatus 1 comprises a vacuum pad 5 to be affixed for sucking directly over a package box 3, a suction tube 7 for connecting the vacuum pad 5 in communication with a vacuum source, such as a vacuum pump (not shown), an inspection arm 9 supporting the vacuum pad 5, a rotating shaft 11 for rotatably supporting the inspection arm 9, a driving device 13 for driving the rotating shaft 11, and a torque sensor 15 for detecting a torque induced in the driving device 13. Respective components are carried by a predetermined frame 17 (see FIG. 2), so that they can move along with the frame 17. It is to be noted that although the rotating shaft 11, the driving device 13 and the torque sensor 15 have been illustrated as if they were not fixedly arranged in FIG. 1, just for the purpose of convenience of the description, actually the rotating shaft 11 is fixedly supported by means of a set of bearings and a housing of the driving device 13 is also fixedly arranged so as not to rotate. Each of the components as designated above will now be individually described.

[Vacuum Pad]

The vacuum pad 5 is made of flexible material such as rubber and has a substantially conical shape. The vacuum pad 5 is sized to have a diameter smaller than a width of each flap 4 of the package box 3 at respective ends thereof (along the vertical direction in FIG. 1), such that the vacuum pad 5 can be entirely affixed for sucking on the surface of the flap 4. The site in which the vacuum pad 5 is affixed for sucking is a region of adhesion with a hot-melt adhesive. Although FIG. 1 shows two vacuum pads to be affixed for sucking on the upper flap 4, by way of simplified illustration only, in an actual practice, another two vacuum pads are similarly to be affixed on the lower flap 4. Additionally, four of the vacuum pads 5 are similarly to be affixed for sucking on the upper and the lower flaps in the opposite side of the package box 3, though not shown. Accordingly, every single package box 3 is provided with a total of eight vacuum pads to be affixed for sucking (see FIG. 3).

[Suction Tube]

The suction tube 7 will now be described. The suction tube 7 is a tubular member in communication with the vacuum pad 5 via the inspection arm 9, which will be described later. The suction tube 7 is coupled with a vacuum source (a vacuum pump) and the communication with the vacuum source is permitted or blocked by an operation of a controller which is not shown. This allows to generate a sucking force in the vacuum pad 5 or inversely to eliminate the sucking force therefrom. The vacuum pad 5 is carried by the inspection arm 9 and makes a rotational movement during the inspection process, and so it is preferred that the sucking tube 7 is made of flexible material. Specifically, the tubular member made of rubber or plastic may be preferred. However, it is required that the tubular member should have a sufficient rigidity so as not to be collapsed due to the decompression that may be applied inside the tubular member. It is to be appreciated that although the suction tube 7 is coupled to the vacuum pad 5 via the inspection arm 9 in the illustrated embodiment, the present invention is not limited to this but the suction tube 7 may be coupled directly with the vacuum pad 5. Further, in addition to the suctioning operation, a back flow of the air may be introduced in the suction tube 7 so as to disengage the vacuum pad 5 positively from the package box 3. In this case, a positive pressure is applied inside the suction tube 7.

[Inspection Arm]

The inspection arm 9 will now be described. The inspection arm 9 is a bar member extending vertically and carrying said vacuum pad 5 in one end thereof (a lower end in FIG. 1). On the other hand, the other end of the inspection arm 9 is coupled to a predetermined block member 10. The rotating shaft 11 is fitted through the block member 10. Accordingly, the inspection arm 9 is adapted to make a rotational movement associatively as the rotating shaft 11 rotates. It is to be appreciated that the inspection arm 9 may be joined to the rotating shaft 11 directly without using the block member 10.

[Rotating Shaft]

The rotating shaft 11 will now be described. The rotating shaft 11 is positioned away from the package box 3 by a predetermined distance and arranged so as to extend in substantially parallel with the flaps 4. In addition, the rotating shaft 11 is supported by a set of bearings which is not shown and only permitted to rotate.

[Driving Device]

The driving device 13 will now be described. The driving device 13 according to the present embodiment is a servomotor, which is coupled to one end of the rotating shaft 11 to drive the rotating shaft 11 to rotate. The servomotor 13 is adapted to detect a rotation angle and is capable of outputting the detected rotation angle as an angle signal to an external device. The angle signal is sent to the controller which is not illustrated, where the rotation angle is computed. It is to be noted that the housing of the servomotor is fixed with use of a predetermined fastener means so as not to rotate.

[Torque Sensor]

The torque sensor 15 will now be described. The torque sensor 15 is coupled to the servomotor 13 and adapted to detect the torque induced in the rotating shaft 11 and output the torque information to an external device. The torque to be detected herein is such a torque that may be generated when the vacuum pad 5 is affixed for sucking on the flap 4 and then the inspection arm is driven to move backward toward its retracted position, as will be described later, wherein the defective adhesion can be detected based on the torque information. To do this, a signal relating to the torque of interest is also sent to the controller.

[Others]

In addition to the main components as described above, though not essential, a peel-off detecting device (not shown) may be separately arranged for detecting the peeling-off of the flap 4 in the present embodiment. Although many different types of peel-off detecting device may be contemplated, an optical sensor (not shown) may be arranged in the vicinity of the inspection arm in the present embodiment. This optical sensor comprises a light source and a light receiver and is adapted such that if the flap in the adhered area is peeled off by more than a predetermined amount during the inspection of the adhesion, the light from the light source to the light receiver may be intercepted. This interception of the light indicates the defective adhesion that has been detected. Alternatively, a CCD camera may be used to capture an image around the flap so that the captured image is image-processed to detect the peeling-off of the flap.

[Inspection Procedure]

An inspection procedure by the adhesion inspection apparatus 1 according to the present embodiment will now be described.

Figure 2:
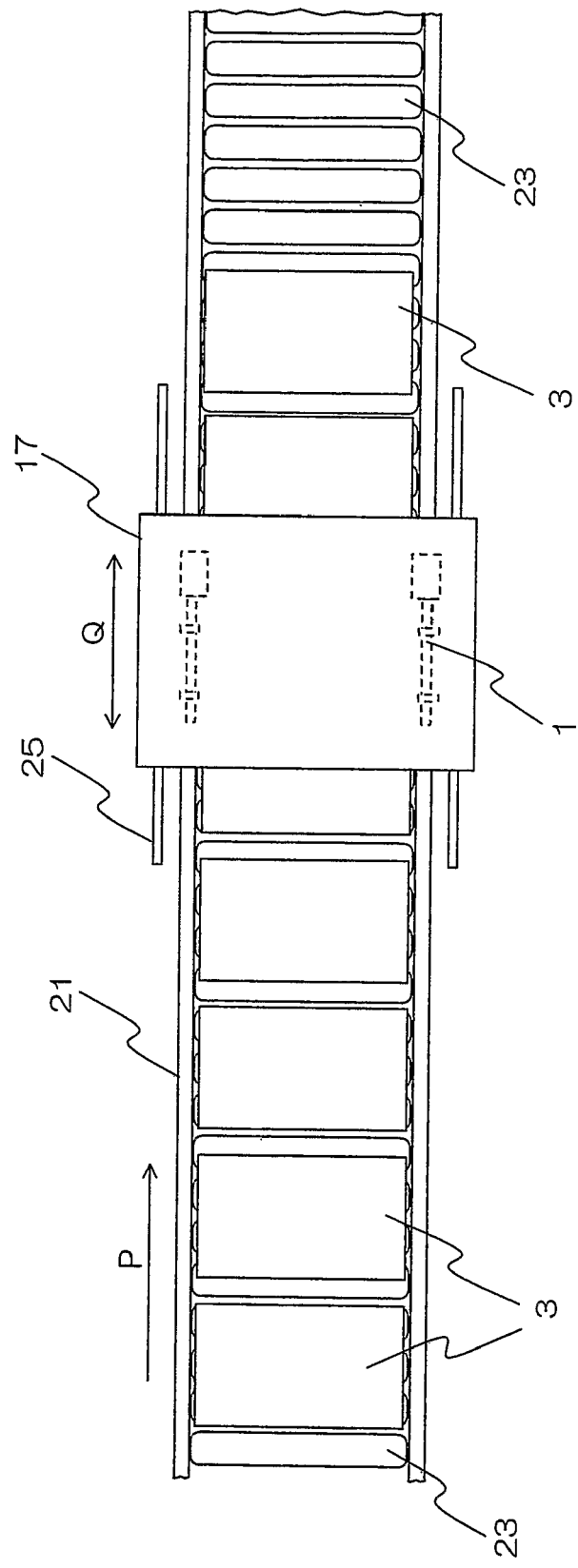
FIG. 2 is a schematic plan view showing an adhesion inspection apparatus arranged on a packaging line.

FIG. 2 is a plan view of a packaging line 21 along with the adhesion inspection apparatus 1 and the frame 17. The adhesion inspection apparatus 1 according to the present embodiment is installed in the packaging line 21 as shown in FIG. 2. In FIG. 2, the package box 3 is moving continuously from the left to the right over a roller conveyer 23 (in a direction shown by an arrow P in FIG. 2). On the other hand, the adhesion inspection apparatus 1 is carried by the frame 17 so as to make a reciprocating movement along a rail 25 aligned in parallel with the frame 17 (along a course shown by an arrow Q in FIG. 2). When the adhesion is actually inspected, the adhesion inspection apparatus 1 moves toward the downstream side with respect to the packaging line 21 at the same speed as the package box 3. This makes a relative speed between the package box 3 and the adhesion inspection apparatus 1 equal to zero, allowing the inspection procedure to be executed. Once the inspection of one package 3 has been completed, the adhesion inspection apparatus 1 moves to the upstream side with respect to the packaging line 21 and back to a position of following another package box 3, on which the same inspection procedure is repeated.

Figure 3:
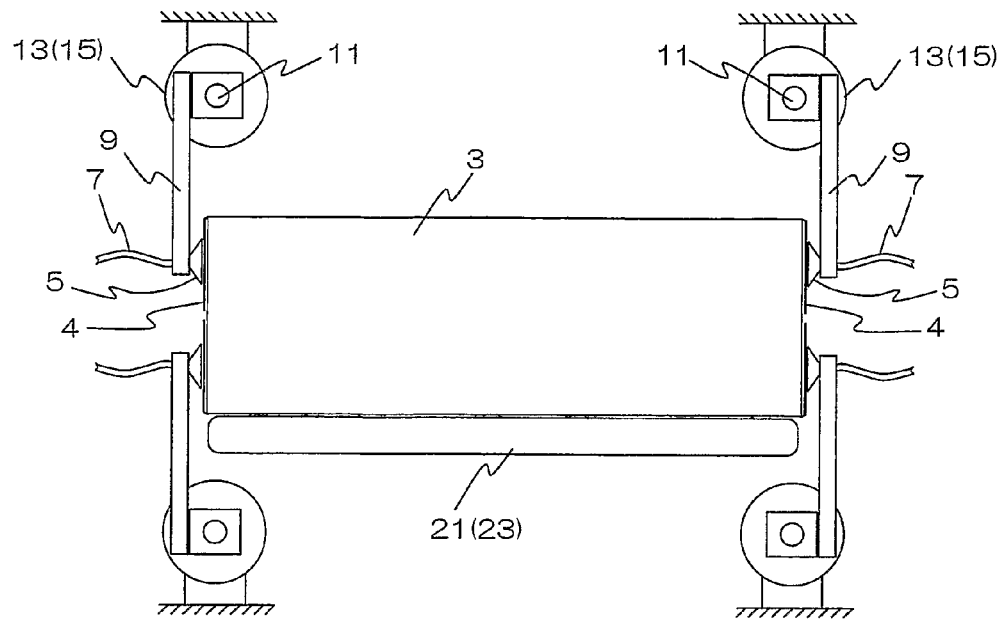
FIG. 3 is an elevational view of an adhesion inspection apparatus viewed from the upstream side with respect to the packaging line.
Figure 4:
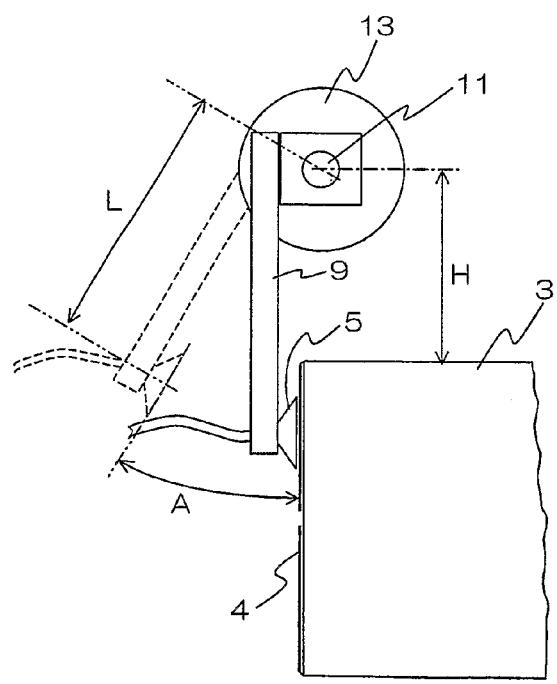
FIG. 4 is a side elevational view illustrating an operation of an adhesion inspection apparatus.

FIG. 3 is a schematic elevational view of the package box 3 and the adhesion inspection apparatus 1 viewed from the upstream side toward the downstream side with respect to the packaging line 21. As shown in this FIG. 3, the package box 3 will have the vacuum pads 5 affixed for sucking on an upper left, a lower left, an upper right and a lower right positions of flaps 4, respectively. Accordingly, since each flap 4 has the two vacuum pads 5 affixed thereon for sucking, a total of eight vacuum pads 5 are affixed for sucking on a single package box 3. The vacuum pad 5 is carried by the inspection arm 9, and the inspection arm 9 is configured to rotationally move in the direction away from the package box 3 in association with the rotation of the servomotor 13. In this connection, the adhesion inspection apparatus 1 is configured to have a length L of 85 mm from a rotation center of the inspection arm 9 to a center of the vacuum pad 5 and a distance H of about 50 mm from the same rotation center to a top surface of the package box 3 as shown in FIG. 4. It is to be noted that this is provided by way of example only, but the length L and the distance H may be appropriately determined for the size of the particular package box 3.

Figure 5:
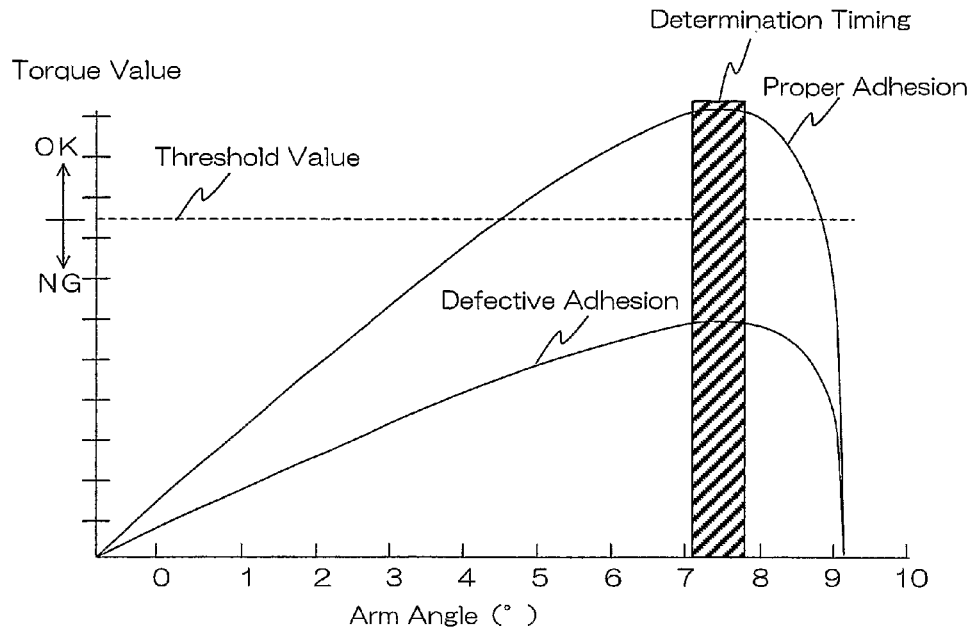
FIG. 5 is a chart illustrating a principle of inspection of an adhesion inspection apparatus according to the present invention.

FIG. 5 is a chart illustrating a relation between an angle A of the inspection arm 9 and a torque value detected in the torque sensor 15. In the chart, a horizontal axis represents the angle of the inspection arm 9 and a vertical axis represents the torque value. The chart presents the case of proper adhesion being provided and the case of defective adhesion. For the package box 3 having the proper adhesion, the torque value is increased and over a threshold value in association with the rotation of the inspection arm 9. As in this condition, if the inspection arm 9 is further rotated, a maximum torque value can read. If the inspection arm 9 is still further rotated beyond the maximum torque value, then the bonded area is peeled off and the torque value starts to decrease. On the other hand, in case of the defective adhesion, although a profile of a curve is basically similar to that of the one having the proper adhesion and the torque value increases in association with the rotation of the inspection arm 9, a maximum torque value does not reach to the threshold value, and the torque value starts to decrease thereafter.

In the inspection of the adhesion under the condition of the present embodiment, the maximum torque value can read when the angle of the inspection arm 9 is in a range of 7 to 8 degrees both for the proper adhesion and for the defective adhesion, as shown in FIG. 5. Based on this, if the determination of the defective adhesion by the adhesion inspection is given over the above-described range of angle, the defective adhesion could be detected accurately. It is to be noted that the threshold torque to be established may be determined through a number of experiments.

Figure 6:
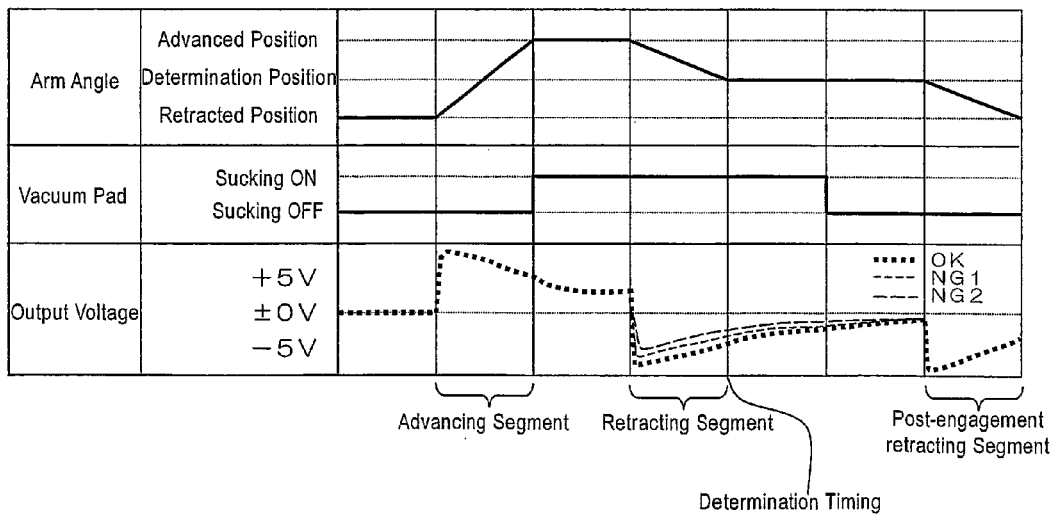
FIG. 6 is another chart illustrating a specific behavior of an adhesion inspection apparatus according to the present invention.

A specific procedure of inspection will be described, given the configuration and inspection principle as described above. FIG. 6 presents a table indicating a relationship between a position of the inspection arm 9 (arm angle), on/off of the sucking operation through the vacuum pad 5, and an output voltage from the torque sensor 15, in which the time elapses toward the right hand side on the table. Initially, at the first stage, the angle of the inspection arm 9 is in a retracted position (for example, A=10 degrees in FIG. 4). During this stage, since the vacuum pad 5 is not in contact with the package box 3, the sucking-off state is indicated. In addition, since there is no torque induced, the output voltage is zero.

Secondly, during an advancing segment in the second stage, the inspection arm 9 approaches to the package box 3 such that the angle of the inspection arm 9 is in the advanced position (A=0 degree in FIG. 4). In this stage also, the vacuum pad 5 is in the sucking-off state. It is to be noted that the output voltage for the torque value is generated in association with the rotation of the inspection arm 9. However, since the actual inspection has not yet started, the output voltage generated therein can be ignored.

Subsequently, in the third stage, the angle of the inspection arm 9 reaches the advanced position (for example, A=0 degree in FIG. 4). Accordingly, the vacuum pad 5 comes into contact with the package box 3 on the predetermined area, and the vacuum pad 5 is now in the sucking-on state. At this time, since the inspection arm 9 remains stopped, the output voltage for the torque value is not much different from that in the previous segment. The area of the package box 3 on which the vacuum pad 5 is affixed for sucking is the region of adhesion by the adhesive such as the hot-melt adhesive.

In the subsequent fourth stage (retracting segment), the servomotor 13 is actuated to rotate and thereby to retract the inspection arm 9. At this time, since the vacuum pad 5 is still in the sucking-on state, the torque is generated in the attempt to keep the inspection arm 9 staying in the vicinity of the package box 3 and thus the output voltage corresponding to that is generated. Then, if the inspection arm 9 reaches a position corresponding to the timing of determination, the servomotor 13 and thus the inspection arm 13 are stopped. The output voltage from the torque sensor 15 at this timing is then detected.

In the subsequent fifth stage, the inspection arm 9 is held at the fixed angle and the vacuum pad 5 is left in the sucking-on state. As it is, after a predetermined time period having past, thus the procedure comes to the end of the determination process, and now in the sixth stage, the inspection arm 9 is held at the fixed angle, while the vacuum pad 5 is placed in the sucking-off state. This cancels the restriction of the inspection arm 9 from the package box 3 and the output voltage for the torque value is decreased to zero.

Finally, in the seventh stage, the inspection arm 9 returns back to its initial retracted position, and thus a series of inspection processes is now completed. Once the first time of the series of inspection processes has been done, the adhesion inspection apparatus 1 is transferred to the upstream with respect to the packaging line 21 and starts to execute the inspection processes on another package box 3, as previously described. It is to be noted that the package box 3 that has been determined as the one having the defective adhesion can be removed from the packaging line 21 at a downstream location.

FIG. 6 presents a graphical representation of an output voltage for the proper adhesion (OK) and the defective adhesion (NG1, NG2). Repeating a large number of experiments to determine the threshold value for the output voltage enables the inspection of the adhesion to be provided in an accurate manner only with the output voltage from the torque sensor 15.

Additionally, in order to improve the inspection accuracy far more, the present embodiment has been provided with a peel-off detection device (not shown). This peel-off detection device is disposed in the vicinity of the inspection arm 9 and capable of detecting an event of the flap 4 in the defective adhesion departing from the package box 3. The use of such a peel-off detection device can reinforce the detection of the defective adhesion and help to provide a reliable detection by working supplementary even in case of failure of the defective adhesion detection with use of the torque value.

The present invention has been described with reference to the adhesion inspection by utilizing a positive control to the sucking-on and -off condition of the vacuum pad 5, but the present invention is not limited to this. For example, the sucking power of the vacuum pad 5 may be set to produce a certain level of torque such that the pad could disengage from the properly bonded flap but could not disengage from the defectively bonded flap. With the sucking power set into this level, the vacuum pad tends to disengage from the properly bonded package box by itself during the inspection processes, contributing to simplifying the sucking-on and -off control.

Further, as shown in FIG. 4, the center of rotational movement of the upper flap 4 of the package box 3 upon being peeled off is located at a corner in the upper left of the package box 3. In contrast to this, the center of rotational movement of the inspection arm 9 is located at much above level than the corner by a distance, H. In this arrangement, although the flap 4 and the inspection arm 9 are placed in the parallel relationship when they are oriented in the vertical direction, the difference between the angle of the inspection arm 9 and the angle of the flap 4 would increase, as the inspection arm 9 rotates. In case of such an angular difference being generated, if occurring in the package box 3 having the defective adhesion, similarly such a great torque that could be produced in the proper adhesion case may be observed upon disengagement of the vacuum pad 5 from the flap 4. Thus, if a large torque occurred in spite of the actual condition of defective adhesion, the accurate inspection of the adhesion would be no more provided.

In order to solve the above problems, the distance H from the rotation center of the flap 4 to the rotation center of the inspection arm 9 should be set minimum. Specifically, it is preferred that the rotation axis 11 should be located as closely to respective corners of the package box 3 as possible.

The present invention is applicable to a means used in a direct inspection of adhesion in a package box and the like constructed with use of an adhesive.

The invention claimed is:

1. An adhesion inspection apparatus for inspecting adhesion of a package box constructed with use of an adhesive, comprising:
    a vacuum pad for sucking an outer surface of said package box at an area proximal to an adhered region;
    an inspection arm carrying said vacuum pad at one end of said inspection arm;
    a rotating shaft joined to the other end of said inspection arm;
    a driving device for driving said rotating shaft to make a rotational movement; and
    a torque sensor for detecting a torque induced in said driving device.

2. The adhesion inspection apparatus claimed in claim 1, wherein said vacuum pad is connected with a suction tube in communication with a vacuum source.

3. The adhesion inspection apparatus claimed in claim 1, wherein said rotating shaft is coupled with at least two sets of said vacuum pad and said inspection arm.

4. The adhesion inspection apparatus claimed in claim 1, wherein said rotating shaft is parallel with an axial line of a rotational movement of a flap of said package box, which is triggered when said adhered region of said package box is peeled off.

5. The adhesion inspection apparatus claimed in claim 4, wherein said rotating shaft is disposed proximal to said axial line of a rotational movement.

6. The adhesion inspection apparatus claimed in claim 1 characterized in that a peel-off detection device capable of detecting peeling-off of said package box is disposed in the vicinity of said inspection arm.

7. An adhesion inspection method using said adhesion inspection apparatus claimed in claim 1.

8. The adhesion inspection method claimed in claim 7, comprising the steps of:
    sucking said outer surface of said package box by said vacuum pad;
    retracting said inspection arm from said package box by said rotational movement of said driving device;
    detecting a value of torque which is induced in said driving device when said inspection arm is in a predetermined angular position; and
    determining an adhesion to be defective, if said torque value is not greater than a predetermined value.

9. The adhesion inspection method claimed in claim 7, wherein during said step of sucking said outer surface of said package box by said vacuum pad, air is suctioned from said vacuum pad through said suction tube.

10. The adhesion inspection method claimed in claim 1, wherein during said step of determining an adhesion to be effective or defective, said torque value is detected with said inspection arm fixed in a predetermined angular position.

11. The adhesion inspection apparatus claimed in claim 1, wherein sucking power of said vacuum pad is in such a magnitude that as said inspection arm is retracted, said pad could disengage from said outer surface of said box having proper adhesion but not disengage from an outer surface of said box having defective adhesion.

12. The adhesion inspection method claimed in claim 1, wherein sucking power of said vacuum pad is in such a magnitude that as said inspection arm is retracted, said pad could disengage from an outer surface of said box having proper adhesion but not disengage from an outer surface of said box having defective adhesion.

13. The adhesion inspection apparatus claimed in claim 1, wherein the inspection is carried out for the box continuously moving in a packaging line.

* * * * *